United States Patent

Ilardi et al.

[19]

[11] Patent Number: 5,961,992
[45] Date of Patent: Oct. 5, 1999

[54] BENEFIT AGENT COMPOSITIONS COMPRISING MIXTURES OF ALPHA-HYDROXY ESTERS

[75] Inventors: Leonora Ilardi, Englewood, N.J.; Michael Paul Aronson, West Nyack, N.Y.; Ronni Weinkauf, River Edge, N.J.

[73] Assignee: Lever Brothers Company Inc., New York, N.Y.

[21] Appl. No.: 08/898,237

[22] Filed: Jul. 22, 1997

[51] Int. Cl.[6] .................................................. A61K 7/48
[52] U.S. Cl. .................... 424/401; 424/70.1; 424/70.19; 424/70.21; 424/70.22; 424/70.27; 424/70.31; 514/532; 514/546; 514/552; 514/844
[58] Field of Search .................. 424/401, 70.1, 424/70.19, 70.21, 70.22, 70.27, 70.31; 514/546, 552, 532, 844

[56] References Cited

U.S. PATENT DOCUMENTS

| | | | |
|---|---|---|---|
| 4,224,339 | 9/1980 | Van Scott et al. | 424/289 |
| 4,234,599 | 11/1980 | Van Scott et al. | 424/279 |
| 4,529,605 | 7/1985 | Lynch et al. | 514/552 |
| 4,540,567 | 9/1985 | Oneto et al. | 424/45 |
| 5,002,680 | 3/1991 | Schmidt et al. | 252/90 |
| 5,180,579 | 1/1993 | Birtwistle et al. | 424/70 |

FOREIGN PATENT DOCUMENTS

95/05160   2/1995   WIPO .

OTHER PUBLICATIONS

A Study to Assess the Moisturizing Keratolytic, Antiacne and Antiageing Effect of Alpha–Alpha–Hydroxy Acid Esters by L. Celleno et al., pp. 277–308.

*Chemical Pharmacy Bulletin* 38 (*1990*) pp. 2877–2879–Enchancing Effects of Myristyl Lactate and Lauryl Lactate on Percutaneous Absorption of Indomethacin in Rats by Dohl et al. (Chemical Abstract vol. 114, 1991, also included).

*British Journal of Dermatology* (1784) 110, pp. 475–485–The Mode of Action of Ethyl Lactate as a Treatment for Acne by Prottey et al.

Primary Examiner—Jyothsna Venkat
Attorney, Agent, or Firm—Ronald A. Koatz

[57]  ABSTRACT

The present invention relates to skin care or personal wash cleanser compositions comprising mixtures of short and long-chain alpha-hydroxy acid esters in order to obtain long term benefit of shorter esters while masking short term drying effect of short chain esters.

11 Claims, 9 Drawing Sheets

FIG.7

| EFFECT MEASURED (COMPARED TO VEHICLE) | 1.6% CETYL LACTATE | 1.6% CETYL LACTATE + 1% OCTYL (S)-LACTATE | 1.6% (S)-LACTIC ACID |
|---|---|---|---|
| VISUAL DRYNESS | SIGNIFICANTLY LESS DRY AT WEEK 8 | PARITY THROUGH TREATMENT; DIRECTIONALLY LESS DRY AFTER SOAP CHALLENGE | SIGNIFICANTLY LESS DRY FROM WEEKS 1-4 & AFTER CHALLENGE (P=0.02) |
| TOTAL CERAMIDE LEVELS | PARITY | DIRECTIONAL INCREASE (AT 80% CONFIDENCE INTERVAL) | SIGNIFICANT INCREASE; 199% |

BENEFIT AGENT COMPOSITIONS COMPRISING MIXTURES OF ALPHA-HYDROXY ESTERS

BACKGROUND OF THE INVENTION

The present invention relates to personal wash cleanser compositions comprising an a-hydroxy benefit agent which in turn comprises mixtures of both short chain ($C_2$–$C_{10}$) and long chain ($C_{11}$–$C_{24}$) a-hydroxy acid esters. More specifically, by combining the longer term moisturizing effect of short chain esters, (note, short chain esters such as butyl (S)- or octyl (S)-lactate often have initial drying effect) with the shorter term moisturizing/masking benefit of long chain esters (e.g., octadecyl (S)-lactate), applicants have obtained superior compositions. Mixing both short and long term moisturizing effects allows compositions to be prepared which have long term beneficial effects while providing short term visual tactile effects of soft, smooth skin. More specifically, applicants have been able to mix short chain esters (normally drying) with long chain esters and significantly reduce the drying effect of the short chain esters while providing longer term moisturizing effects associated with the shorter chain esters.

The use of short chain α-hydroxy acid esters (e.g., $C_1$ to $C_4$ alkyl lactates to treat acne) or long chain α-hydroxy acid esters (e.g., long chain lactate ester emollient) is broadly taught in the art. No art, however, teaches a specific combination of long and short chain esters of α-hydroxy acid (e.g., lactic acid) or that, in combination, the long and short chain esters could provide multiple benefits.

U.S. Pat. No. 4,540,567 to Oneto et al. (assigned to Lever Brothers), for example, teaches compositions comprising short chain $C_1$–$C_4$ alkyl lactate (primarily for treatment of acne) or mixtures which are dissolved in a mixture of water and water-miscible $C_2$–$C_4$ alkylene glycol or a polymer thereof. Alkylene glycol is said to act as a vehicle to help limit dehydration of skin and improve sensory feel of product. There is no teaching or suggestion of combining with long chain a-hydroxy acid esters or that by doing so dehydration effect can be ameliorated.

U.S. Pat. No. 5,002,680 to Schmidt et al. teaches mild skin cleansing aerosol mousse compositions with skin feel and moisturization benefits. Among the moisturizers which can be used are taught non-occlusive moisturizers (including lactic acid esters) and occlusive moisturizers (e.g., petrolatum, mineral oil) in formulations comprising surfactant, polymeric skin feel aid and propellant. The lactic acid esters are taught generally, but there is no teaching or suggesting of mixing long chain and short chain α-hydroxy acid esters or any teaching or suggestion that one (short term benefit of long chain esters) may complement the possible deficiencies (i.e., short chain esters may be drying in the short term even though providing longer term benefit) of the other.

U.S. Pat. No. 4,529,605 to Lynch teaches a bathing oil composition comprising a nonionic surfactant, a cationic surfactant and a primary emollient which may be a long chain lactate ester. There is no teaching of short chain esters or of combinations of long and short chain esters.

U.S. Pat. No. 4,234,599 to Van Scott et al. relates to a method of treating dry skin by topically applying a composition (e.g., cream, ointment) containing alpha or beta hydroxy acids or esters thereof. Specific mixtures of long and short chain α-hydroxy acid are neither taught nor suggested.

In "A Study to Assess the Moisturizing Keratolytic Antiacne and Antiaging Effect of Alpha-Alpha-Hydroxy acid Esters" by L. Celleno, A. Vasseli, M V. Tolaini, G. Serafina, G, Ferte, C. Gemona (In Cosmetics' Exhibition & Conference, Paris, France, Apr. 5–7, 1995), the beneficial effects of various alpha-hydroxy esters is taught. Again, however, there is no teaching or suggestion of using short chain and long chain esters in the same composition.

In International Publication WO 95/05160 (assigned to Unilever), there is taught cleanser formulation containing esters of hydroxy alkanoic acid as conditioners. There is no teaching or suggestion of using mixtures of short and long chain α-hydroxy acid esters or that the two should be simultaneously used to provide dual benefits.

It is thus one object of the invention to provide a unique composition which provides the long term moisturizing benefits provided by short chain length α-hydroxy acids while at the same time masking the short term dryness often caused by the short chain esters by using long chain esters of α-hydroxy acids to provide short term moisturizing benefits.

SUMMARY OF THE INVENTION

Suddenly and unexpectedly, applicants have found that specific mixtures of short chain and long chain α-hydroxy acid esters provide dual benefit (short and long term moisturizing benefit) previously difficult or impossible to obtain.

More specifically, the invention relates to personal wash compositions comprising:
 (a) 0% to 90% by wt. composition of a surfactant selected from the group consisting of anionic surfactants, nonionic surfactants, amphoteric surfactants, cationic surfactants and mixtures thereof; and
 (b) 1% to 25% by wt. composition, preferably 1% to 15% by wt. of a benefit agent composition comprising:
  (i) 0.01% to 10% branched or unbranched, saturated or unsaturated, straight or cyclic $C_2$ to $C_{10}$ α-hydroxy acid esters; and
  (ii) 0.01% to 10% branched or unbranched, saturated or unsaturated, straight or cyclic $C_{11}$ to $C_{24}$, preferably $C_{14}$ to $C_{22}$ α-hydroxy acid esters; and
  (iii) balance water
 wherein said benefit agent composition (b) comprises at least 0.5% combined (i) and (ii).

In one embodiment, the composition is a liquid personal wash composition comprising:
 (a) 5 to 60%, preferably 10 to 40% by wt surfactant;
 (b) 1 to 25%, preferably 1 to 15% by wt. α-hydroxy mixture benefit agent composition;
 (c) 0 to 25%, preferably 1 to 15% by wt. structurant;
 (d) 0 to 15% by wt. thickening or thinning agent;
 (e) 1 to 20% by wt. additional emollient; and
 (f) balance water.

In a second embodiment of the invention, the composition is a cosmetic composition comprising:
 (a) 0 to 30% by wt., preferably 1 to 15% surfactant;
 (b) 1 to 25% α-hydroxy acid mixture benefit agent composition; and
 (c) 0.01 to 90% by wt. of a cosmetic composition comprising:
  (i) optional actives (e.g., sunscreens, tanning aids);
  (ii) optional essential fatty acids;
  (iii) 0.5 to 50% by wt. total composition emollient;
  (iv) 0 to 20% by wt. total composition thickener.

BRIEF DESCRIPTION OF THE FIGURES

FIG. 7 shows that lactic acid alone increased lipid production while long chain ester alone does not. Since mixture of esters shows directional increase in lipid production, this again shows benefit of short chain ester (lipid production) is achieved while benefit of long chain ester (masking drying effect of short chain ester) is simultaneously found.

DETAILED SUMMARY OF THE INVENTION

Figure 1:
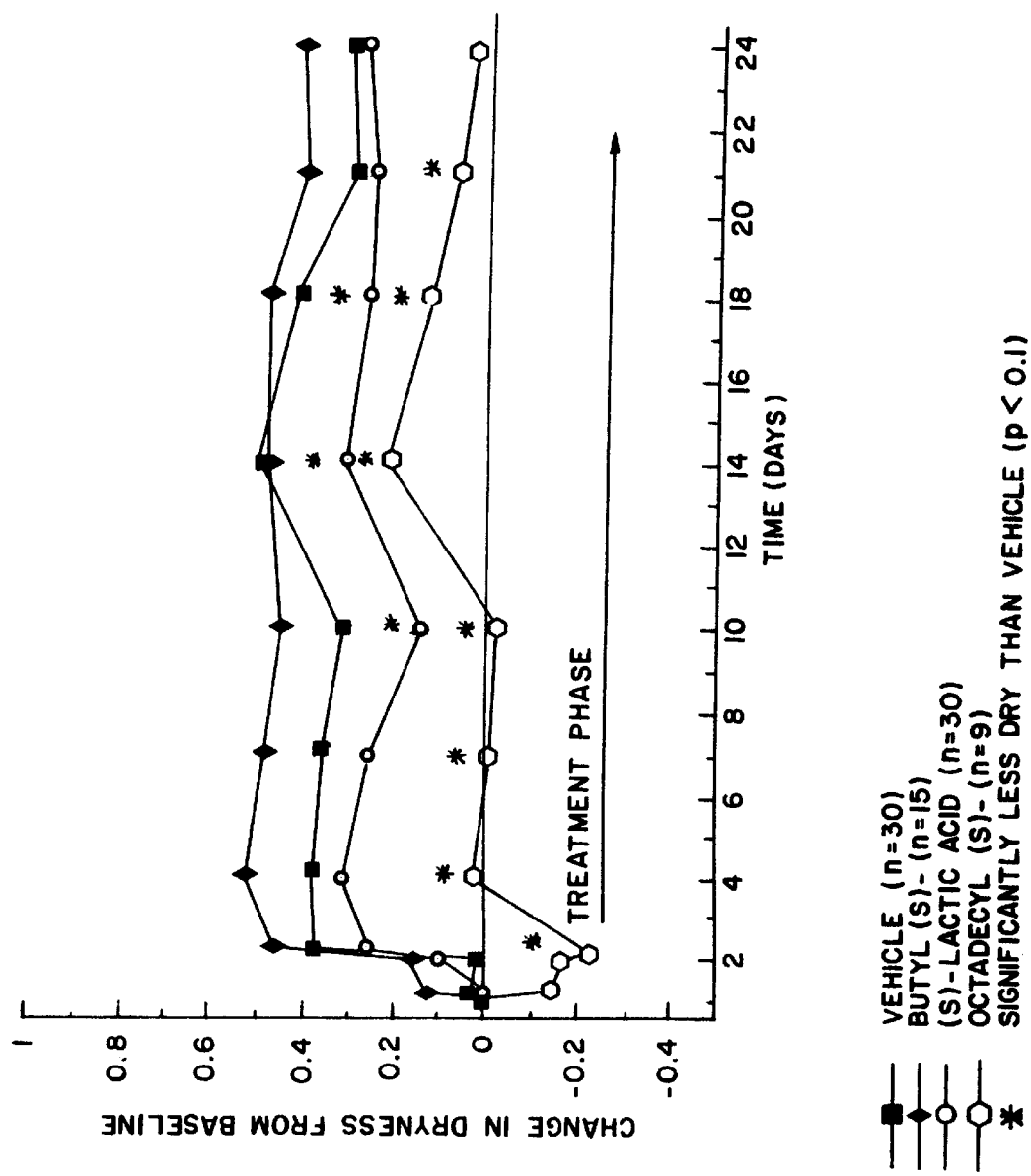
FIG. 1 shows that it is really only the long chain ester which is generally non-drying and that the short chain esters when used alone, have a drying effect. Nonetheless, it is desirable to incorporate short chain esters because they hydrolyze to lactic acid more quickly than long chain esters and deliver long term benefits associated with lactic acid (See Example 1).

The present invention relates to compositions intended to provide both long term and short term moisturizing benefits to the skin. Compositions may be compositions such as creams and cosmetic lotions for the skin, or they may be rinse-off compositions such as shower gels.

More specifically, short chain length α-hydroxy acid esters provide long term moisturizing benefits as well as other benefits (e.g., antiacne) to the skin. However, the short chain α-hydroxy acid esters also cause skin drying in the short term. Thus, it would be greatly beneficial to deliver long term moisturizing benefit to the skin (i.e., through short chain esters of hydroxy acid) while at the same time masking or eliminating the short term dryness effect.

Unexpectedly, applicants have found that the desired benefits can be obtained by providing compositions having a specific combination of long and short chain α-hydroxy acid esters.

BENEFIT AGENT COMPOSITION (CONTAINING MIXED ESTERS)

Esters

The compositions of the invention comprise a mixture of short and long chain alpha-hydroxy esters. The α-hydroxy benefit agent compositions are aqueous compositions suitable for topical application to skin or hair comprising:

(a) 0.01% to 10% by weight of a $C_2$ to $C_{12}$ branched or unbranched, saturated or unsaturated, straight or cyclic ester of alpha hydroxy acid or mixtures of said short chain esters;

(b) 0.01% to 10% by wt. of a $C_{14}$ to $C_{24}$ branched or unbranched, saturated or unsaturated, straight or cyclic ester of α-hydroxy acid or mixtures of said long chain esters; and (c) balance water.

The combination of (a) with (b) must be at a minimum 0.5% of the benefit agent composition; preferably at least 2.0%.

An α-hydroxy acid (AHA) generally is an organic carboxylic acid in which there is a hydroxy group at the two, or alpha (α), position to the carbonyl moiety. Examples of such α-hydroxy acids are glycolic and lactic acid.

Examples of short chain esters of α-hydroxy acid include $C_1$ to $C_{10}$ alkyl lactates such as methyl (S)-lactate, butyl (S)-lactate, octyl (S)-lactate, etc. Cyclic esters such as benzyl (S)-lactate are also contemplated. The esters may be of other α-hydroxy acids such as esters of glycolic acid, citric acid, malic acid, tartaric acid, tartronic acid, mandelic acid, α-hydroxybutyric acid, α-hydroxyisobutyric acid, α-hydroxy valeric acid, mucic acid, galacturoic and saccharic acid (glucaric acid), saccharic acid 1,4,-lactone, atrolactic acid and phenyl lactic acid. Although S isomers are generally preferred (e.g. S-isomer of lactic acid is naturally occurring isomer in the skin), it should be noted that R isomers or racemic mixtures may also be used in the invention.

A preferred short chain ester is octyl (S)-lactate.

Example of long chain esters of α-hydroxy acid include $C_{14}$ to $C_{22}$ alkyl lactates such as tetradecyl (S)-lactate, cetyl lactate etc. Again esters may be of other α-hydroxy acid such as esters of glycolic acid, citric acid, malic acid, tartaric acid, tartronic acid, mandelic acid, α-hydroxybutyric acid, α-hydroxyisobutyric acid, α-hydroxy valeric acid, mucic acid, galacturoic and saccharoic acid, saccharic acid (glucaric acid), saccharic acid 1,4,-lactone, atrolactic acid and phenyl lactic acid.

Preferred long chain ester include bcetyl lactate, octadecyl (S) lactatekor behenyl (S)-lactate.

Preferred mixtures of long chain and short chain might include $C_8$ lactic acid ester and $C_{18}$ lactic acid ester.

Preferably the short chain ester will comprise 0.01% to 10% of the benefit agent compositions; and preferably the long chain ester will comprise 0.01% to 10% of the benefit agent composition, with water comprising the balance.

Whether used in personal wash compositions or cosmetic compositions, the benefit agent compositions will generally comprise about 1 to 25% of the composition. This is not fixed, however, and depends on the exact make-up of the personal wash or cosmetic composition. What is critical is only use of the benefit agent compositions in these personal wash or cosmetic bases.

Water

The benefit agent composition of the invention comprises an amount of water to act as a vehicle for the esters and to enable them to be provided at a concentration suitable for convenient topical application to skin.

The amount of water present in the benefit agent composition of the invention is accordingly up to 99%, preferably from 50% to 99% by weight of the benefit agent composition.

In addition to short and long chain esters of the various recited acids and to water, the benefit agent vehicle may comprise small amounts of other ingredients such as preservatives, antimicrobial agents, thickeners pH adjusting agents, and other skin modifying or skin benefit agents (e.g. polysiloxanes).

For example, the carrier composition may comprise 0.01 to 1%, preferably 0.02 to 0.5% of a preservative such as dimethyloldimethylhydantoin (DMDM hydantoin), DMDM plus 3-iodo-2-propyl butyl carbamate (Glycdant Plus®); formaldehyde, Kathan® from Rhone Poulenc; parabens etc..

Thickeners in the carrier would be used at about 0.01 to 2%, preferably 0.1 to 1% of the carrier and include ingredients such as guar gums (e.g., hydroxypropyl guar guam) or cross-linked polyacrylate polymers (e.g., Carbopol® polymer from B. F. Goodrich).

Among pH adjusting agents which may be used in the carrier include sodium hydroxide, phosphoric acid, citric acid and succinic acid. Again, these will comprise from 0.01 to about 2% of the carrier.

Other ingredients which may be used in the carrier include perfumes, dyes, sequestering agents (e.g., EDTA), suspending agents (e.g., Mg/H silicate) and/or skin feel and skin benefit agents (e.g., silicone, essential fatty acids, petrolatum, etc.).

BASE COMPOSITIONS

As noted, the benefit agent compositions (ester mixtures and carrier compositions including water) may be used in either a personal wash liquid cleansing base or in cosmetic composition base.

Surfactant

The compositions according to the invention may optionally contain surfactant depending on product form. More specifically, personal wash compositions, for example, will generally comprise 5 to 60%, preferably 10 to 40% surfactant, while cosmetic compositions need not comprise any surfactant, but preferably comprise 1% to 30% by wt., more preferably 1 to 15% by wt. surfactant.

Examples of surfactants include anionic surfactants as well as nonionic, amphoteric and zwitterionic surfactants. Preferred personal wash compositions comprise mixtures of anionic and amphoteric surfactants. Surfactants which may be used, in either personal wash or cosmetic compositions, are described in greater detail below.

Anionics

The compositions according to the invention can optionally comprise, as a surfactant one or more soaps which are water-soluble or water-dispensable alkali metal salts of an organic acid, especially a sodium or a potassium salt, or the corresponding ammonium or substituted ammonium salt. Examples of suitable organic acids are natural or synthetic alkanoic acids having from 10 to 22 carbon atoms, especially the fatty acids of triglyceride oils such as tallow and coconut oil. For solid products, such as powders, bars or tablets, the preferred soap is a soap of tallow fatty acids, that is fatty acids derived from tallow class fats, for example beef tallow, mutton tallow, lard, palm oil and some vegetable butters. Minor amounts of up to about 30%, preferably 10 to 20%, by weight of sodium soaps of nut oil fatty acids derived from nut oils, for example coconut oil and palm kernel oil, may be admixed with the sodium tallow soaps, to improve their lathering and solubility characteristics if desired. Whereas tallow fatty acids are predominately $C_{14}$ and $C_{18}$ fatty acids, the nut oil fatty acids are of shorter chain length and are predominantly $C_{10}$–$C_{14}$ fatty acids.

For liquid or gel products, the preferred soap are predominantly $C_{10}$–$C_{14}$ fatty acids derived from nut oils, or alternatively, from synthetic alkanoic acids.

The soaps can be provided as a performed ingredient for the composition, or they can be formed in situ during the manufacture of the composition by reaction of suitable fatty acids and an alkali.

The amount of fatty acid soap which can be present in the composition according to the invention is up to 90%, preferably from 2 to 80% by weight of the composition.

The composition according to the invention can also optionally comprise one or more non-soap anionic surfactants, examples of which include:

The alkali metal salts of organic sulfuric reaction products having an alkyl or acyl radical containing from 8–22 carbon atoms and a sulphonic acid or sulfuric acid ester group. Specific examples of these synthetic anionic surfactants are the sodium, ammonium, potassium or triethanolammonium alkyl sulphates, especially those obtained by sulphating the higher alcohols ($C_8$–$C_{18}$), sodium coconut oil fatty acid monoglyceride sulphates and sulphonates; sodium or potassium salts of sulfuric esters of the reaction product of one mole of a higher fatty alcohol (e.g., tallow or coconut oil alcohols) and 1–12 moles of ethylene oxide; sodium or potassium salts of alkylphenol ethylene oxide ether sulphate with 1–10 units of ethylene oxide per molecule and in which the alkyl group contains from 8 to 12 carbon atoms, sodium alkyl glyceryl ether sulphonates, the reaction product of fatty acids having from 10 to 22 carbon atoms esterified with isethionic acid and neutralized with sodium hydroxide; water soluble salts of condensation products of fatty acids with N-methyl taurine. Especially preferred non-soap anionic surfactants include:

alkylaryl sulphonates, such as sodium alkyl benzene sulphonate (e.g., TEEPOL CM44, available from Shell), alkyl sulphates, such as sodium lauryl sulphate (e.g., EMPICOL CX, available from Albright & Wilson), and triethanolamine lauryl sulphate (e.g., EMPICOL TL40/T, available from Albright & Wilson);

alkyl ether sulphates, such as sodium lauryl ether sulphate (e.g., EMPICOL ESB70, available from Albright & Wilson);

alkyl sulphonates, such as sodium alkane (C13–18) sulphonate (e.g., HOSTAPUR SAS 30, available from Hoechst);

olefin sulphonates, such as sodium olefin sulphonate (C15–18) (e.g., HOSTAPUR OS, available from Hoechst);

Sarcosinates, having the structure (3):

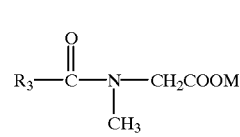

where $R_3$ is chosen from $C_{6-14}$ alkyl, and

M is a counterion chosen from alkali metals, ammonium, substituted ammonium, such as alkanolammonium.

An example of sarcosinates having the structure (3) sodium lauryl sarcosinate (e.g., HAMPOSYL L-95, available from Grace).

Taurides, having the structure (4):

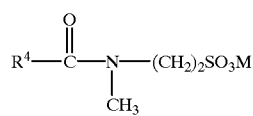

where
$R^4$ is chosen from $C_{8-18}$ alkyl.

An example of taurides having the structure (4) is: coconut methyl taurine (e.g., FENOPON TC 42, available from GAF).

Isethionates, having the structure (5)

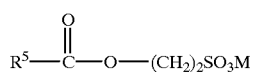

where
$R^5$ is chosen from $C_{8-18}$ alkyl.

An example of isethionates having the structure (5) is: sodium acyl isethionate (e.g., JORDAPON Cl, available from Jordan).

Monoalkyl sulphosuccinates, having the structure (6):

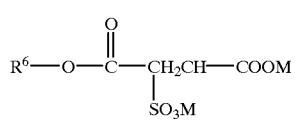

where
$R^6$ is chosen from $C_{10-20}$ alkyl.

Examples of monoalkyl sulphosuccinates having this structure (6) include: sodium lauryl sulphosuccinate (e.g., EMPICOL SLL, available from Albright & Wilson); magnesium alkyl sulphosuccinate (e.g., ELFANOL 616 Mg, available from AKZO), sodium lauryl ethoxysulphosuccinate (e.g., EMPICOL SDD, available from Albright & Wilson), coconut monoethanolamide ethoxysulphosuccinate, (e.g., EMPICOL SGG); disodium lauryl polyglycol ether sulphosuccinate (e.g., SURTAGENE S30, available from CHEM-Y) polyethyleneglycol sulphosuccinate (e.g., REWOPOL SBFA 30, available from REWO). Dialkyl sulphosuccinates, having the structure (7):

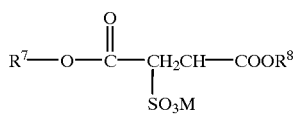

where
$R^7$ and $R^8$ are the same or different, and are chosen from $Cr_{6-14}$ alkyl.

an example of dialkyl sulphosuccinate having the structure (7) is: sodium dioctyl sulphosuccinate (e.g. EMCOL 4500 available from Witco).

Acyl lactylates, having the structure (8):

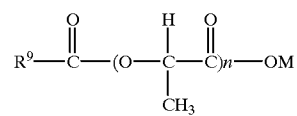

where
$R^9$ is chosen from $C_{6-16}$ alkyl.

An example of acyl lactylates having the structure (8) is: decanoyl lactylate (e.g., PATIONIC 122A, available from Patterson, C. J.).

Acylated a-amino acids, such as sodium lauryoyl glutamate (e.g., ACYL GLUTAMATE LS-11, available from Ajinomoto Co. Inc.).

Ethyl carboxylates, such as alkyl $C_{12-14}$ $O(EO)_4OCH_2CO_2Na$ (e.g., AKYPO RLM 38, available from AKZO).

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

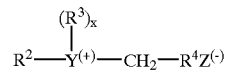

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl) ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and 5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

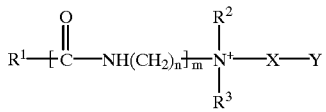

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is —$CO_2$— or —$SO_3$—

Suitable amphoteric detergents within the above general formula include simple betaines of formula:

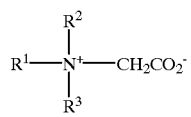

and amido betaines of formula:

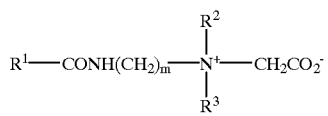

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

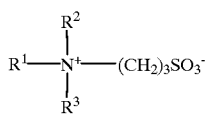

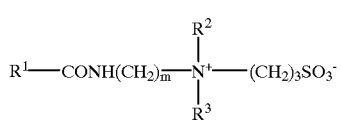

where m is 2 or 3, or variants of these in which —$(CH_2)_3SO^-_3$ is replaced by

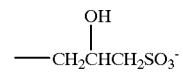

In these formulae $R^1$, $R^2$ and $R^3$ are as discussed previously.

Amphoacetates and diamphoacetates are also intended to be covered in possible zwitterionic and/or amphoteric compounds which may be used.

Amphoteric/zwitterionic, when used, generally comprises 0 to 25%, preferably 0.1 to 20% by wt. of the composition.

The surfactant system may optionally comprise a nonionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula

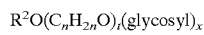

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Nonionic comprises 0 to 10% by wt. of the composition.

LIQUID PERSONAL WASH COMPOSITIONS

If present in liquid personal wash composition, the surfactant system of the invention may comprise 5% to 60% by wt., preferably 10–40% by wt. of a surfactant system which preferably comprises:

(a) 1% to 20% by wt. one or more anionics as described above;

(b) 0.1 to 20% by wt. amphoteric/zwitterionic;

(c) 0 to 10% nonionic surfactant.

Anionics, amphoteric/zwitterionic and nonionics are as described above. In a preferred system, the anionic is acyl isethionate and amphoteric is betaine such as cocoamidoalkylbetaine.

Such personal wash compositions may optionally include structurant. Suitable structuring materials include swelling clays, for example laponite; fatty acid and derivatives thereof, in particular, fatty acid monoglyceride polyglycol ethers; cross-linked polyacrylates such as Carbopol™ (polymers available from Goodrich); acrylates and copolymers thereof; polyvinylpyrrolidone and copolymers thereof; polyethyleneimines; salts such as sodium chloride and ammonium sulphate; sucrose esters; gellants; and mixtures thereof.

Of the clays, particularly preferred are synthetic hectorite (laponite) clay used in conjunction with an electrolyte salt capable of causing the clay to thicken. Suitable electrolytes include alkali and alkaline earth salts such as halides, ammonium salts and sulphates.

The composition may also comprise internal lamellar phase-inducing structurants. Such structurants include $C_8$–$C_{24}$ unsaturated and/or branched liquid fatty acid or esters thereof; $C_8$–$C_{24}$ unsaturated and/or branched liquid alcohol or ether thereof; and/or $C_5$ to $C_9$ fatty acids wherein those structuring have MP below 25° C.

When present, structurants may comprise 0.1 to 25%, preferably 1 to 15% of composition.

The personal wash formulations may also comprise a thickening (or thinning) agent, i.e., a material which maintains the viscosity of this phase as the shear rate thereof is increased during use. Suitable materials include cross-linked polyacrylates such as Carbopol™ (polymers available from Goodrich); natural gums including alginates, guar, xanthan and polysaccharide derivatives including carboxy methyl cellulose and hydroxypropyl guar; propylene glycols and propylene glycol oleates; salts such as sodium chloride and the ammonium sulphate; glycerol tallowates; and mixtures thereof.

These agents may comprise 1% to 15% by wt. of the composition.

Other typical components of such compositions include opacifiers, preferably 0.2 to 2.0 wt.%; preservatives, preferably 0.2 to 2.0 wt. %; and perfumes, preferably 0.5 to 2.0 wt. %. Cationic polymers such as Jaguar® from Rhone Poulenc and Polymer JR® from Amerchol may also be included.

The base compositions may further comprise additional oil/emollient particles (particularly when in lamellar phase) wherein the additional benefit agent (i.e., in addition to the α-hydroxy acid mixture benefit agent composition) may be as set forth below:

Vegetable oils: Arachis oil, cannola oil, castor oil, cocoa butter, coconut oil, corn oil, cotton seed oil, olive oil, palm kernel oil, rapeseed oil, safflower seed oil, sesame seed oil and soybean oil.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate.

Animal Fats: Acytylatelte lanolin alcohols, lanolin, lard, mink oil and tallow.

Fatty acids and alcohols: Behenic acid, palmitic acid, stearic acid, behenyl alcohol, cetyl alcohol, eicosanyl alcohol and isocetyl alcohol.

Other examples of oil/emollients include mineral oil, petrolatum, silicone oil such as dimethyl polysiloxane, lauryl and myristyl lactate.

Additional emollient/oil generally will comprise, if present, 1% to 20% of the composition.

Other ingredients which may be found in such personal care compositions are as follows:

Organic solvents, such as ethanol; auxiliary thickeners, such as carboxymethylcellulose, magnesium aluminum silicate, hydroxyethylcellulose, methylcellulose, carbopols, glucamides, or Antil® from Rhone Poulenc; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic conditioners which may be used include Quatrisoft LM-200 Polyquaternium-24, Merquat Plus 3330 - Polyquaternium 39; and Jaguar® type conditioners.

Polyethylene glycols which may be used include:

| Polyox | WSR-205 | PEG 14M, |
| Polyox | WSR-N-60K | PEG 45M, or |
| Polyox | WSR-N-750 | PEG 7M. |

Other thickeners which may be used include Amerchol Polymer HM 1500 (Nonoxynyl Hydroethyl Cellulose); Glucam DOE 120 (PEG 120 Methyl Glucose Dioleate); Rewoderm® (PEG modified glyceryl cocoate, palmate or tallowate) from Rewo Chemicals; Antil® 141 (from Goldschmidt).

Another optional ingredient which may be added are the defloculating polymers such as are taught in U.S. Pat. No. 5,147,576 to Montague, hereby incorporated by reference.

Another ingredient which may be included are exfoliants such as polyoxyethylene beads, walnut sheets and apricot seeds

COSMETIC COMPOSITIONS

If present as a cosmetic "leave-on" composition, the compositions generally will contain less surfactant (i.e., 0–30%, preferably 1–15% by wt.) but include more ingredients characteristic of cosmetic or commercially acceptable vehicle. For example, the benefit agent composition will comprise 1 to 25% by wt. of the total composition, surfactant may comprise 0.5 to 30% by wt. of the composition and balance will be cosmetic vehicle composition.

The cosmetic vehicle composition (comprising 1% to 99% of total cosmetic, preferably 1–80% of total cosmetic)

may comprise an oil or oily material, together with an emulsifier, to provide either a water-in-oil emulsion or an oil-in-water emulsion, depending largely on the average hydrophilic-lipophilic balance (HLB) of the emulsifier employed.

Various types of active ingredients may be present in cosmetic vehicle compositions of the present invention. Actives are defined as skin or hair benefit agents other than emollients and other than ingredients that merely improve the physical characteristics of the composition. Although not limited to this category, general examples include sunscreens, tanning agents.

Sunscreens include those materials commonly employed to block ultraviolet light. Illustrative compounds are the derivatives of PABA, cinnamate and salicylate. For example, octyl methoxycinnamate and 2-hydroxy-r-methoxy benzophenone (also known as oxybenzone) can be used. Octyl methoxycinnamate and 2-hydroxy4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Typically actives will comprise 1% to 30% of the total cosmetic composition.

Another preferred optional ingredient is selected from essential fatty acids (EFAs), i.e., those fatty acids which are essential for the plasma membrane formation of all cells, in keratinocytes EFA deficiency makes cells hyperproliferative. Supplementation of EFA corrects this. EFAs also enhance lipid biosynthesis of epidermis and provide lipids for the barrier formation of the epidermis. The essential fatty acids are preferably chosen from linoleic acid, γ-linolenic acid, homo-γ-linolenic acid, columbine acid, eicosa-(n-6, 9, 13)-trienoic acid, arachidonic acid, γ-linolenic acid, timnodonic acid, hexaenoic acid and mixtures thereof.

Emollients are often incorporated into cosmetic compositions of the present invention. Levels of such emollients may range from about 0.5% to about 50%, preferably between about 5% and 30% by weight of the total cosmetic composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate(a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the total composition. Exemplary thickeners are cross-linked polyacrylate materials available under the trademark Carbopol from the B. F. Goodrich Company. Nonionic cellulose materials such as methyl cellulose and hydroxy propyl methyl and cellulose may be used. Also cationic cellulose materials such as polymer JR400 and cationic gums such as Jaguar <135 may be used as thickeners.

Surfactants, which are also sometimes designated as emulsifiers, may be incorporated into the cosmetic compositions of the present invention. Surfactants can comprise anywhere from about 0.5 to about 30%, preferably from about 1 to about 15% by weight of the total composition. Surfactants may be cationic, nonionic, anionic, or amphoteric in nature and combinations thereof may be employed.

The composition according to the invention can also contain other optional adjuncts, that is ingredients other than the main ingredients already defined which are conventionally employed in compositions for topical application to human skin. These adjuncts, when present, will normally form the balance of the composition.

Examples of optional adjuncts include vehicles, the selection of which will depend on the required product form of the composition. Typically, the vehicle when present, will be chosen from diluents, dispersants or carriers for the ingredients so as to ensure an even distribution of it when applied to the skin.

The compositions may include water as a vehicle in combination with at least one other cosmetically-acceptable vehicle.

Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl monolaurate, glyceryl monoricinoleate, glyceryl monostearate, propane-1,2-diol, butane-1,3-diol, docosan-1,2-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, , isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, acetone, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicondioxide, sodium polyacrylate, tetra alkyl and/or trialkyl aryl ammonium smectites, chemically modified magnesium aluminum silicate, organically modified montmorillonite clay, hydrate aluminum silicate, fumed silica, carboxyvinyl polymer, sodium carboxymethyl cellulose, ethylene glycol monostearate.

The cosmetically acceptable vehicle, when present, will usually form from 0.01 to 99.9%, preferably from 50 to 98% by weight of the composition, and can, in the absence of other cosmetic adjuncts, form the balance of the composition.

A typical cosmetic composition will comprise:
(a) 0.05 to 30%, preferably 1 to 15% surfactant;
(b) 1% to 25% α-hydroxy ester mixture benefit agent composition; and
(c) 1 to 98% of a composition which composition comprises of
  (i) 1% to 20% total cosmetic composition of actives;
  (ii) 1% to 15% total composition essential fatty acids;
  (iii) 0.5 to 50% total composition emollient; and
  (iv) 0.1 to 20% total composition thickener.

Product Form

The composition according to the invention can take the form of a liquid or gel, intended to be dispensed from a capped container such as a bottle, roll-on applicator or tube, or a pump-operated or propellant driven aerosol dispenser, as a skin cleanser, shower product, bath additive or shampoo. The composition can also take the form of a powder or a solid such as a stick, preferably housed in a suitable capped holder with a wind-up or push-up action similar to a lip stick, or a bar or tablet, with or without fatty acid soaps, intended to be used for washing instead of a conventional soap bar.

Compositions of the invention may be formulated as products for washing the skin, for example, bath or shower gels, hand washing compositions or facial washing liquids; pre- and post-shaving products; rinse-off, wipe-off and leave-on skin care products; products for washing the hair and for dental use.

The compositions of the invention will generally be pourable liquids or semi-liquids e.g., pastes and will have a viscosity in the range 250 to 100,000 mPas measured at a shear rate $10s^{-1}$ and 25° C., in a Haake Rotoviscometer RV20.

The invention also provides a closed container containing a detergent composition as herein defined.

Process for Preparing the Composition

The invention also provides a process for preparing the composition of the type defined herein, which process comprises the steps of:
(i) preparing a mixture comprising mixture of α-hydroxy acid esters as defined herein;
(ii) combining with surfactant and personal wash ingredients to form personal wash formulation or combining with cosmetic vehicle (optionally comprising surfactant) to form leave-on compositions; and
(iii) packaging personal wash or leave on cosmetic compositions (or other product forms) into containers.

The following examples are intended to further illustrate the invention and are not intended to limit the invention in any way.

EXAMPLES

Example 1

The following test protocol relates to protocol conducted in obtaining information recorded in FIG. 1.

Protocol

For purposes of FIG. 1, the studies evaluated the effect on dry lower leg skin that could be delivered from short chain (S)-lactic acid ester (butyl) versus long chain (octadecyl) and how these effects compared to vehicle alone or lactic acid alone. All compounds were deposited on skin at known dosages.

Subject Screening

The study population was comprised of healthy, female volunteers in general good health between the ages of 18 and 65. Volunteers were self-assessed as being susceptible to developing dry skin of the lower legs in the absence of using a moisturizer. Fifty-three subjects were enrolled in a conditioning phase and thirty subjects qualified for participation in the product application phase of the study.

Study Design

The study was a randomized, double-blind study which utilized an incomplete block design, where each subject served as her own positive and negative control. The study was designed to simulate the effects of washing with a mild cleanser containing a benefit agent which is deposited on the skin at a known level during the wash. The study involved a seven day conditioning phase, in which volunteers discontinued moisturizer use and washed their lower leg for 30 seconds twice a day with a moisturizing composition comprising as follows:

| | |
|---|---|
| Acyl isethionate | 3–10% |
| Sodium laurethsulfate | 1–5% |
| Betaine | 5–15% |
| Perfume, preservative and minors | 1–5% |
| Water | to balance |

Following the conditioning phase, each of the subjects' outer, lower legs were divided into two 120 $cm^2$ (10 cm×12 cm) test sites, for a total of four test sites per subject. Subjects having dryness scores between 1.5–3.0 (inclusive), with no greater than a 1 point difference among all test sites within a subject, entered the four week product application phase of the study. During the product application phase, the subjects performed the product application procedure twice daily, in the morning and evening, approximately 12 hours apart.

As noted above, each subject evaluated lactic acid, vehicle, and the following two ester products: butyl (S)-lactate, and octadecyl (S)-lactate as noted in the Table below:

| Test Material | Concentration | Applied Level of Material ($\mu g/cm^2$) | Applied Level of Lactate ($\mu g/cm^2$) |
| --- | --- | --- | --- |
| Butyl (S)-lactate | 1.46% (0.1M) | 29 | 18 |
| Octadecyl (S)-lactate | 3.42% (0.1M) | 68 | 18 |
| (S)-Lactic acid | 0.9% (0.1M) | 18 | 18 |
| Vehicle | — | — | 0 |

On days 1 and 2 of the product application phase, visual evaluation of dryness and erythema were conducted prior to the morning wash and approximately 6 hours after the morning wash. Subsequent visual evaluations were made on Days 4, 7, 10, 14, 18, 21, and 24, prior to the morning wash. Additional instrumental measurements were obtained on Days 14 and 24.

Product Application Procedure

The product application was conducted by the subject, and the study personnel supervised those treatments which took place at the test center, using the following procedure:

The subject wet both legs (upper, outer calf with warm water. The subject wet hands and dispensed approximately 0.5 g of shower gel (having formulation noted above) into one hand. The subject gently generated a foamy lather in both hands by rubbing hands together for approximately 10 seconds. The subject's right hand washed the right leg and the left hand washed the left leg. The subject gently glided lathered fingers up and down the upper outer calf for thirty seconds, applying equal pressure to both legs. The subject rinsed the lower legs with warm water and patted completely dry with a soft towel. The subject attached the provided fabric template to the outer calf using surgical tape to guide test product application. The subject dispensed approximately 0.25 g (via a dropper bottle) of each test product to the designated 120 cm test sites (2 mg of formulation/cm ), one at a time, and rubbed each gently but thoroughly into the test site, ensuring that none of the test product was rubbed onto any other site other than the designated one.

This entire procedure is be referred to as the "Product Application Procedure" throughout and was conducted twice a day, approximately 12 hours apart. Outside of the scheduled washes, the lower legs were not washed with any of the soap or cleanser or treated with any other moisturizer.

Clinical Evaluation

Visual dryness assessments were conducted by one qualified evaluator prior to the start of the product application phase (baseline) to determine subject qualification. Subsequent visual evaluations were made by the same evaluator as described in the study design section above prior to any wash or product application. Test sites were assessed for dryness using a 0–4 scale with half point increments. The evaluator ranked the sites in case of ties. Erythema was used as a monitor of irritation only. Any test site obtaining a score of 3.5 or greater for dryness or erythema was discontinued from subsequent product application.

Instrumental Assessment

Transepidermal water loss (TEWL) measurements were made using a Servomed Evaporimeter EP1 at each test site. Stratum corneum hydration was determined as a measure of conductance using a SKICON-200 instrument equipped with an MT-8C probe, at each test site. TEWL and conductance measurements were obtained prior to the start of the product application phase (baseline), after two weeks of treatment, and at the end of the study (final).

Materials

The test materials were butyl (S)-lactate, and octadecyl (S)-lactate (pH 7.0) and were compared to (S)-lactic acid (pH 3.5) and vehicle. The vehicle for lactate acid esters was as follows:

| Vehicle for Lactic Acid and Lactic Acid Esters | |
| --- | --- |
| | % Active in Product |
| Preservative | 0.2 |
| $KH_2PO_4$ | 0.4 |
| $K_2HPO_4$ | 0.6 |
| Polysorbate 80 (Tween 80) | 0.4 |
| Deionized Water | to 100 | pH 7.0 +/− 0.5 for esters
pH 3.5 +/− 0.5 for lactic acid

Statistical Analysis

Visual Data

To determine whether any product provided a change in visual dryness from baseline the following was done. At each evaluation point, the Pratt-Lehmann version of the Wilcoxon signed rank test was performed on the difference in clinical grades (evaluation - baseline) for each test product to determine whether the test product provided a significant change from its baseline score and in which direction. To compare the test products, two statistical methods were employed. Method 1: At each evaluation point, the Pratt-Lehmann version of the Wilcoxon signed rank test was conducted on the difference in clinical grades (evaluation - baseline) for each matched-pair of treatments across all groups, using the panelist as a block. Method 2: at each evaluation point, the Wilcoxon rank sum test was conducted on the difference in clinical grades for each pair of treatments, as if the data came from independent groups, ignoring the panelist effect. For data gathered, differences at $p \leq 0.10$ were considered to be statistically significant.

Instrumental Data

The TEWL and conductance measurements for each treatment were analyzed relative to baseline readings, using a two tailed paired t-test. Between treatment comparisons were made on the difference in instrumental values (evaluation - baseline), using a two tailed paired t-test, for each matched-pair of treatments across all groups. At each evaluation to compare both within treatment changes from baseline and between treatment differences, using the panelist as a block.

Using the protocol described above, applicants tested the effect of (1) lactic acid; (2) butyl ester of lactic acid and (3) octadecyl ester of lactic acid on dryness compared to vehicle (with no acid or ester) alone.

As seen from FIG. 1, a short chain ester such as butyl ester (which provides good long term benefits) is as drying as vehicle alone. It is only the long chain ester (e.g., octadecyl ester) which provides significantly less drying.

Notwithstanding the short term drying effects of butyl ester, the ester readily delivers lactic acid and, therefore, is known to provide good long term benefit. For example, lactic acid is known to provide enhanced desquamation of stratum corneum leading to smooth skin (see Scott et al., *Dermatol. Res.* 110:585–592 (1974)); to thicken the epidermis thereby reducing fine lines and wrinkles (Bartolone et al., *J. Invest Dermatol.*, 104:609 (1995)); and to enhance skin lipid biosynthesis in stratum corneum leading to better barrier function (see Rawlings et al., *Arch Dermatol. Res.*, 288:383–390 (1996). Each of these references is hereby incorporated by reference into the subject application.

It should be noted, as seen in Example 4, that the preference for short chain esters (in delivering lactic acid) is that they hydrolyze at a rate greater than longer chain esters and therefore deliver the effects of lactic acid more quickly.

Example 2

As noted, Example 1 and FIG. 1 shows that, despite the multiple benefits of delivering lactic acid, short chain esters are initially drying. Thus, applicants conducted an example to see whether short term drying could be masked by combining short chain esters and long chain esters. The study was conducted as follows:

Study Objective

The objective of this study was to evaluate the effects on lower leg dry skin of combinations of octyl (S)-lactate, octadecyl (S)-lactate, and cetyl lactate in a post-wash product application.

Methodology

This was a randomized, double-blind study utilizing a complete block design, and involved a one week conditioning phase and a 5 day product application phase. The study was completed with 21 female subjects.

Conditioning Phase: Subjects underwent a one week conditioning phase, in which they washed the outer part of the lower legs with formulation of Example 1 twice a day and discontinued moisturizer use (see "Study Design" of Example 1). Following the conditioning phase, the subject's legs were divided into eight 20 cm$^2$ sites, four per leg, and subjects with dryness between 1.5–3.0 (a 1 point difference among the eight sites was required) entered the product application phase.

Product Application Phase: The 5 day product application phase involved twice daily applications, 5–6 hours apart. The product application procedure is as follows: both legs were washed for 30 seconds with same moisturizing composition used in Example 1, patted dry, and then the seven post-wash products were applied to the designated test sites. One site was left untreated. Product application was randomized and balanced across test sites. Visual assessments for dryness and erythema was made prior to each wash/application (see "Clinical Evaluation" of Example 1)

Test Products

The following esters were tested either alone or as mixtures as indicated:

1.0% Octyl (S)-lactate (does=20 μg OL/cm$^2$)

1.7% Octadecyl (S)-lactate (dose=34 μg ODL/cm$^2$)

1.0% Octyl (S)-lactate /1.7% Octadecyl (S)-lactate (dose= 20 μg OL, 34 μg ODL/cm$^2$)

Figure 3:
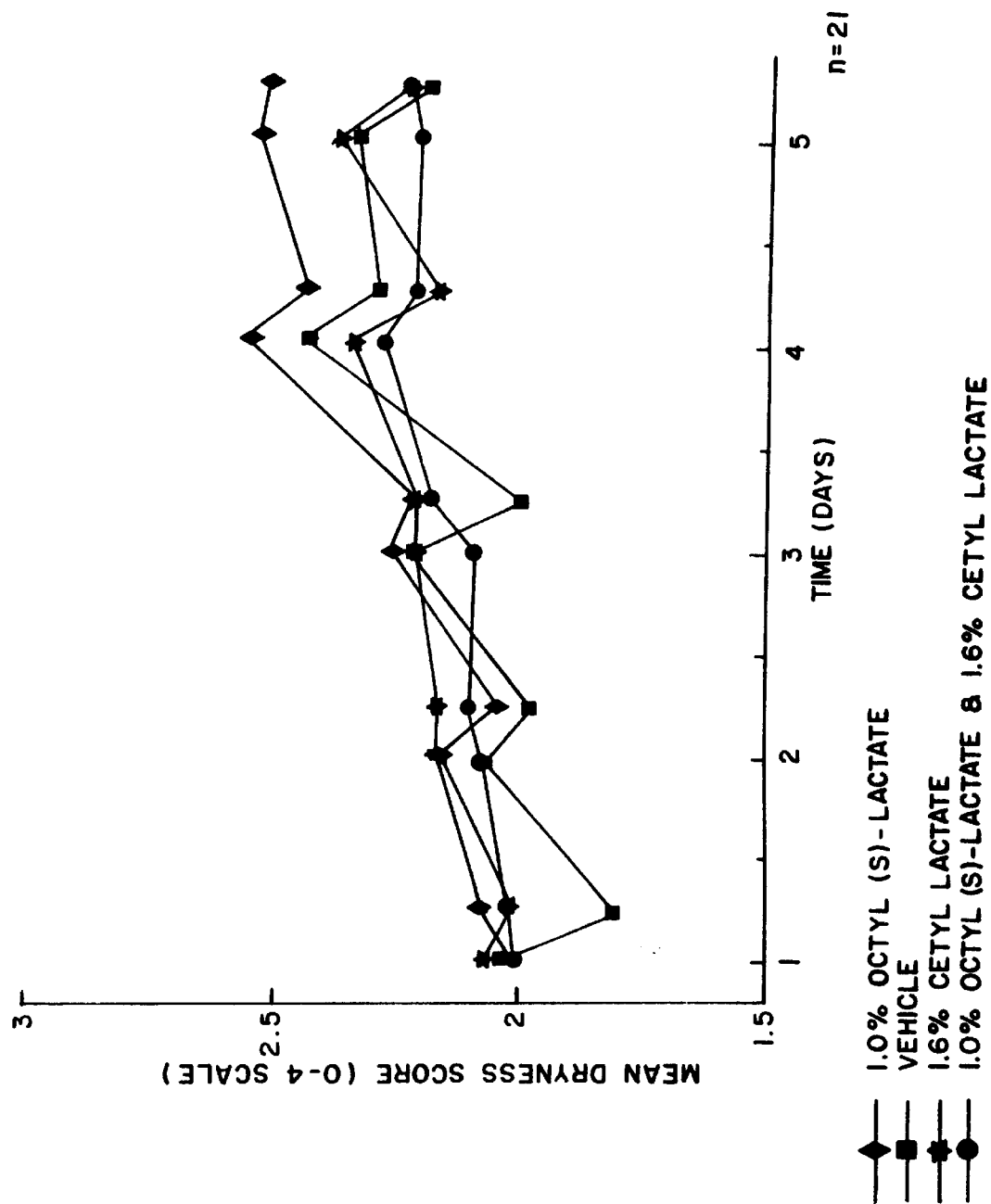
FIG. 3 again shows that, when combined with long chain ester (cetyl lactate), moisturizing effect of long chain ester is not compromised.

3.6% Octadecyl (S)-lactate (dose=72 μg ODL/cm$^2$) (Not shown in FIG. 3)

1.6% Cetyl (S)-lactate (dose - 32 μg CL/cm$^2$)

1.0% Octyl (S)-/1.6% Cetyl lactate (dose=20 μg CL/cm$^2$)

Vehicle

Vehicle for Esters was as Follows 0.45% Trisodium Phosphate, 0.4% Carabomer, 0.4% Pemulen TR2 (acrylic acid/C 10–30 Alkyl Acrylate Cross polymer), 0.1% DMDM Hydantoin, 0.05% Dimethicone Copolyol, Sodium Hydroxide to pH 6.5.

Results

Reduction of visible dryness from baseline was determined for each test product. At each evaluation point, the Pratt/Lehmann version of the Wilcoxon Signed-Rank test was performed on the difference in clinical grades (evaluation session - baseline) for each treatment, using the subject as a block, to determine whether a treatment result was significantly different from its baseline score.

Differences between products in the extent of dryness reduction from baseline was determined for each pair of test products. At each evaluation point, the Pratt/Lehmann version of the Wilcoxon Signed-Rank test was conducted on the difference in clinical grades (evaluation session - baseline) for each pair of treatments, using the subject as a block.

Findings

Figure 2:
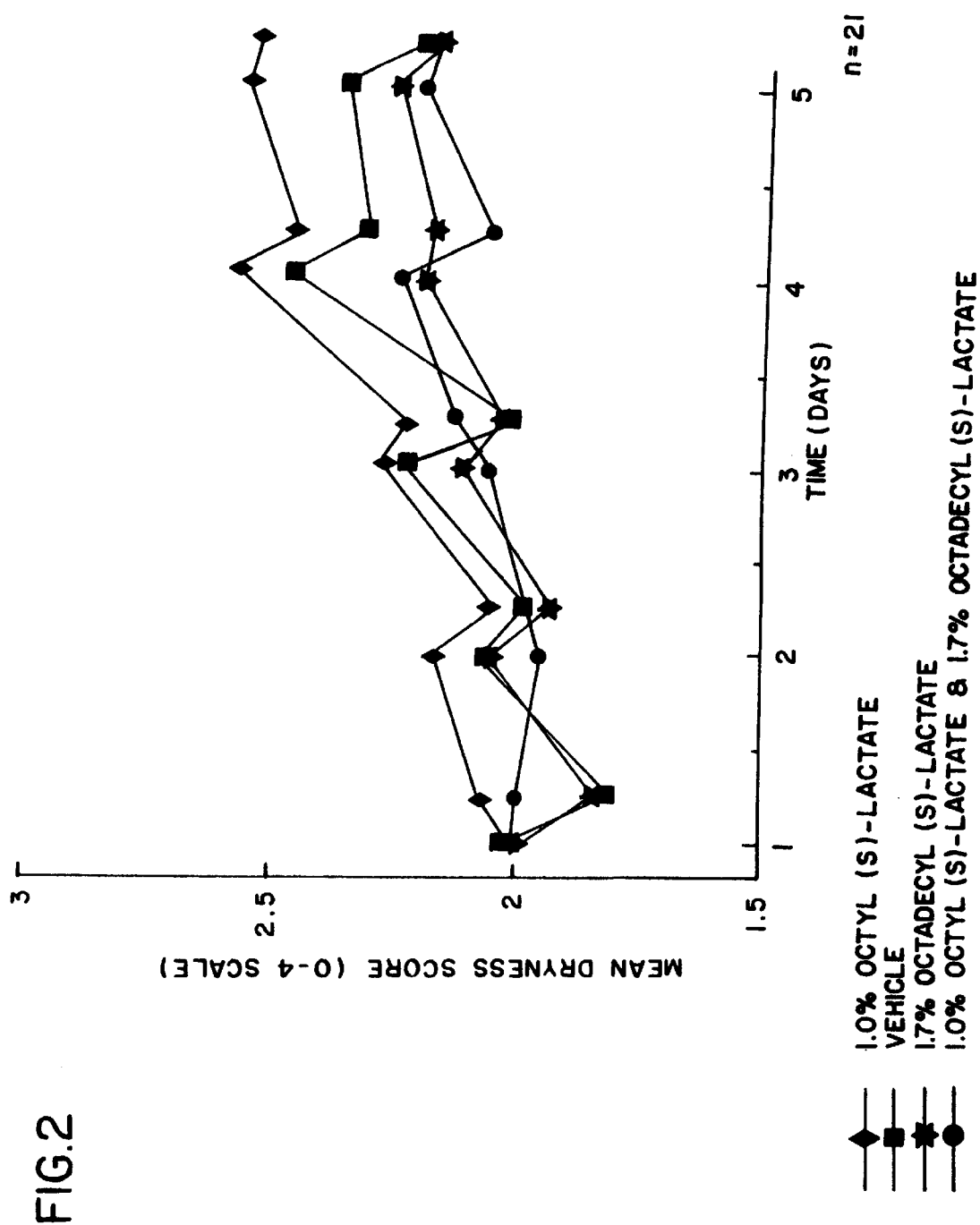
FIG. 2 shows that, quite unexpectedly, when combined with long chain ester, the moisturizing effect of long chain ester (octadecyl (S)-lactate) is not compromised. An advantage of the invention is the ability to retain moisturizing effect of long chain ester without sacrificing long term benefit of short chain ester.

The following findings were made and/or can be seen from FIG. 2 and 3.

(1) 1.0% Octyl (S)-lactate (short chain ester) caused a significant increase in visible dryness (versus baseline). This dryness increase was greater than that observed for vehicle and untreated sites (significance at several time points).

(2) Application of a combination of octyl (S)-/octadecyl (S)-lactate prevents the dryness increase observed for octyl (S)-lactate alone (significance at several time points).

(3) Cetyl lactate (FIG. 3) shows the same trends as octadecyl (S)-lactate in reducing the drying effects of octyl (S)-lactate (significance on Days 4 and 5), however to a lesser degree; and (4) The vehicle itself provided an immediate reduction in visible dryness as observed 6 hours after the first application (Day 1), making it difficult to observe the immediate dryness reduction effects caused by the alkyl lactates. However, over time, the effect of the vehicle was similar to no treatment.

Discussion

It was initially hypothesized that a combination of long chain more slowly penetrating alkyl lactate (e.g., octadecyl (S)-lactate) and shorter chain, more rapidly penetrating alkyl lactate (e.g., octyl (S)-lactate), can provide benefits for dry skin by providing a transient effect on dryness reduction (with long chain ester) and "therapeutic" effect by delivery of lactic acid to the viable epidermis (with short chain ester). Prior to studying the long term effects of combinations of alkyl lactates, it was important to determine whether: 1) low levels of octyl (S)-lactate induces dryness; 2) if so, whether low levels of octadecyl (S)-lactate can prevent the dryness, and 3) if commercially available cetyl lactate (C16) can be utilized in place of octadecyl (S)-lactate. Therefore, this study evaluated the potential of different alkyl lactates to provide a benefit from cleansing, by applying "cleansing relevant" dosages to the skin immediately after it was washed with a mild cleanser.

Specifically, low levels of octyl (S)-lactate (0.05 M or 20 μg/cm$^2$) caused an exacerbation of visible dryness. This was observed immediately after the first treatment, and continued to worsen over the course of the five day study (Example 1). The vehicle utilized in this study actually caused a transient visible dryness reduction in comparison to an untreated site, making it difficult to determine whether "cleansing" levels of octadecyl (S)-lactate or cetyl lactate, alone, provided an immediate reduction in dry skin. However, the vehicle does not appear as though it provides anything more than transient improvements to the skin, since over time the dryness observed on the vehicle treated sites was equivalent to untreated sites and was greater than on sites treated with 3.6% octadecyl (S)-lactate (Not shown in Figure). Octadecyl (S)-lactate and the octyl (S)-/octadecyl (S)-lactate combination provided some effects over that of the vehicle which was evident towards the end of the study. Low levels of octadecyl (S)-lactate were capable of masking the dryness induced by octyl (S)-lactate (FIG. 2), although the magnitude of this effect was fairly small. Cetyl lactate (FIG. 3) was slightly less effective, but provided similar effects for preventing the dryness that is induced by octyl (S)-lactate. While neither long chain ester was capable of providing a reduction in visible dryness during this study, both prevented the drying effects of octyl (S)-lactate, since sites treated with these combinations did not significantly worsen (from baseline) during the study.

The results indicate that combining octyl (S)-lactate with either octadecyl (S)-lactate or cetyl lactate masks its visible drying effects.

Example 3

In order to show the advantage of the mixed chain length esters (octyl(s)lactate/cetyl lactate) versus the long chain ester alone, applicants conducted tests with both and then tested the following in vivo: (1) lipid production (e.g. production of ceramide) for the mixed chain esters versus long chain ester alone (with (S)-lactic acid as comparative); and (2) improvement in barrier function.

Improvement in "barrier" function refers to resistance to increase in dryness when challenged with soap after having been treated with either long chain ester or mixture of long and short chain esters; again using lactic acid (versus vehicle) as comparative.

Generally, the theory given is that lactic acid provides certain biological/chemical effects such as enhancement of lipid production and/or improvement in barrier function; more hydrophobic derivatives of lactic acid (such as esters) would be expected to be delivered more easily; however it is difficult to deliver this material to skin, especially from a wash-off product; if a short chain lactic acid ester hydrolyzes more quickly than a long chain lactic acid ester, one would expect these effects to improve.

Since, however, short chain esters have initial drying effect (FIG. 1), the combination of short chain and long chain esters would allow for the short chain esters to provide the noted benefits while the longer chain esters would provide moisturization to mask the drying effect of the short chain ester.

Barrier Function

To determine whether there was improvement in barrier function, a double blind, randomized, balanced paired comparison of a test product (either long-chain ester alone or short chain/long chain mixture) was tested on one leg and its aqueous vehicle alone was tested on the other using a post wash application protocol, twice daily for 8 weeks. A soap challenge (2 daily washes with Ivory® soap for 5 days) was conducted at end of study to measure barrier resilience and visual, instrumental and biochemical analyses were performed at baseline, 4 and 8 weeks. Six test cells were examined (n=10–12 per cell).

Figure 4:
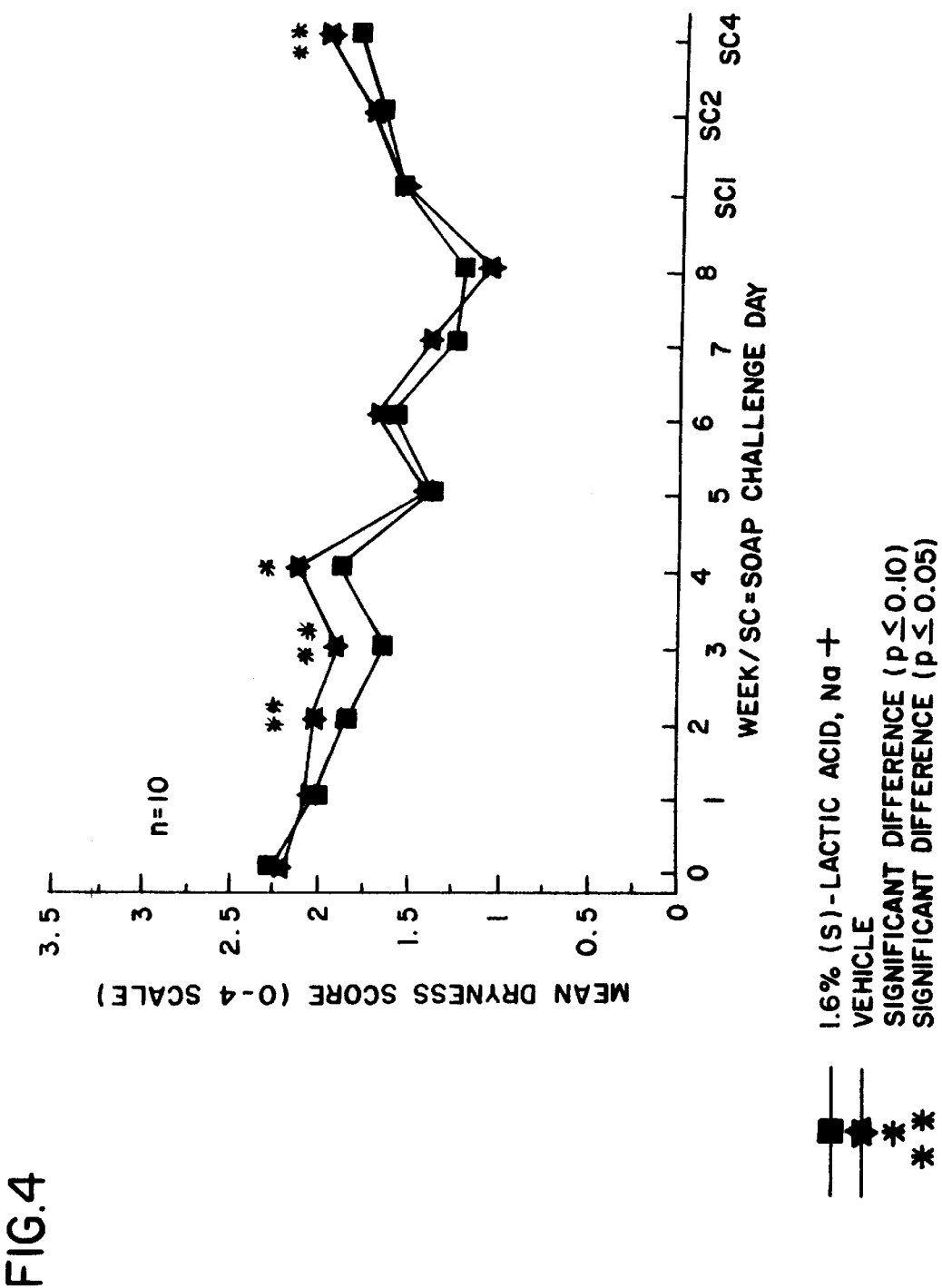
FIG. 4 shows that, after prepping skin for eight (8) weeks with lactic acid, subsequent challenge with soap does not increase dryness. This indicates lactic acid helps skin retain moisture when subsequently challenged by soap, presumably due to enhancement in barrier function.
Figure 5:
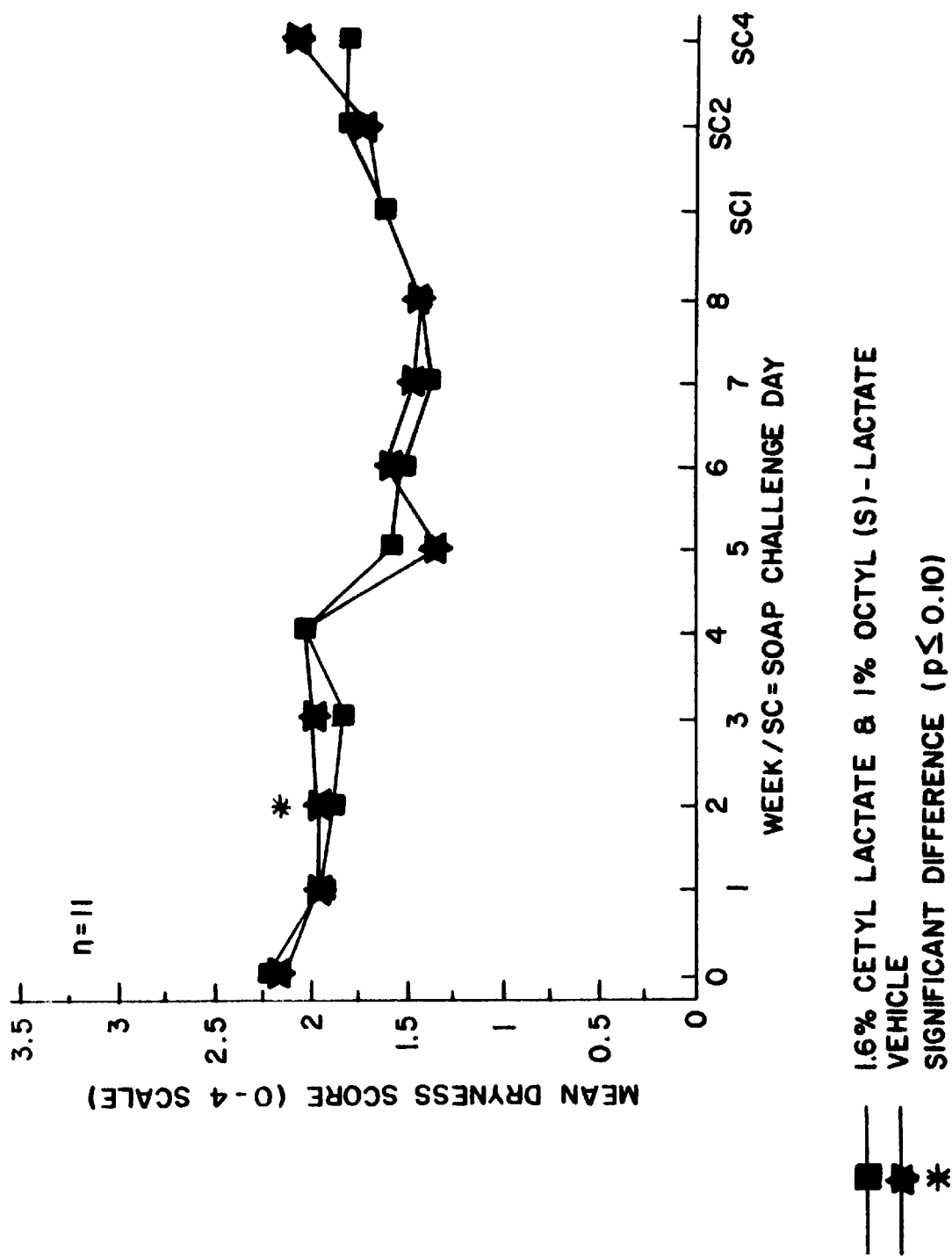
FIG. 5 shows that mixture of long and short chain esters help resist subsequent soap challenge.
Figure 6:
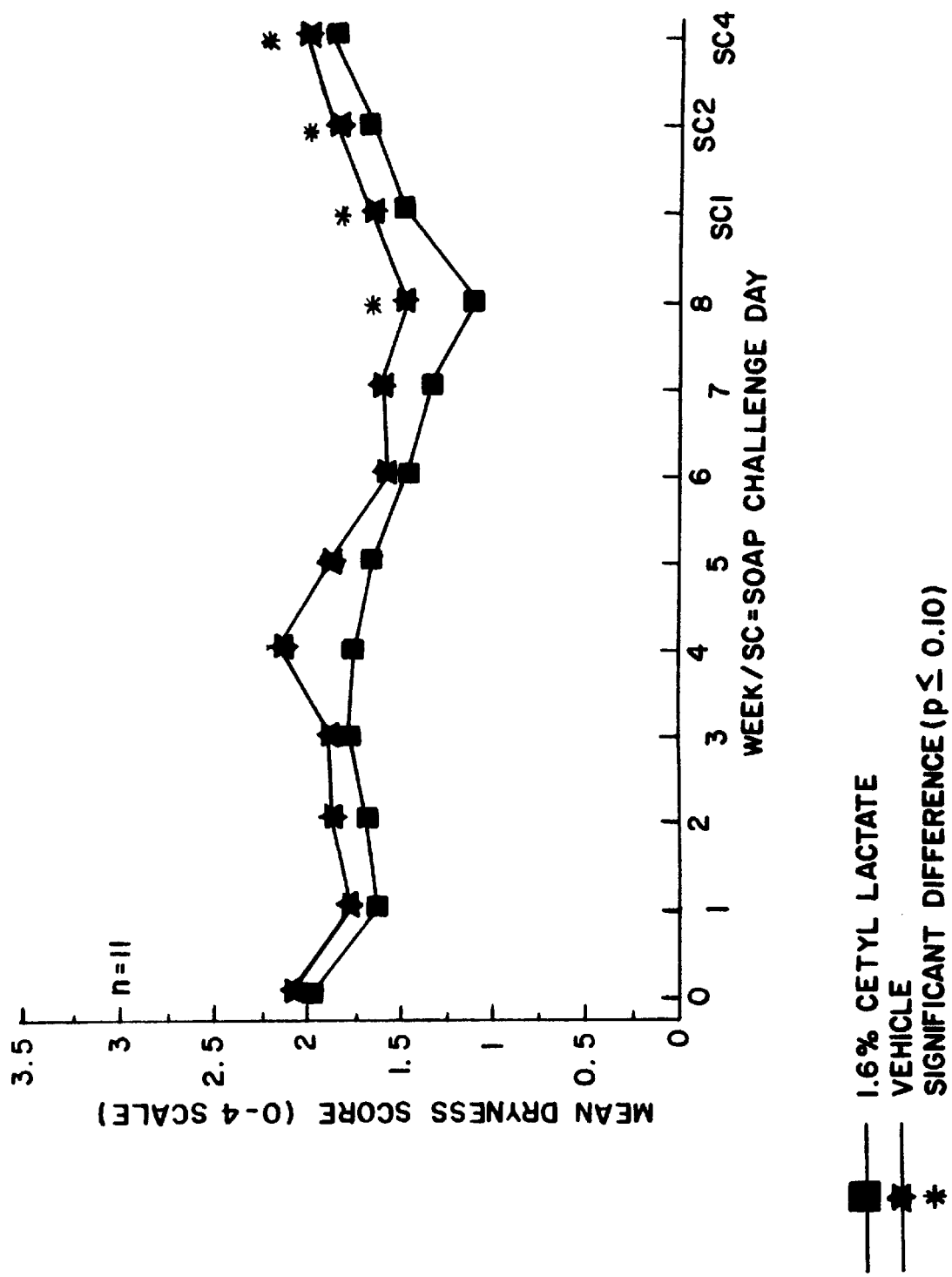
FIG. 6 shows that long chain ester does not resist soap challenge. Together with FIG. 5, this helps show that it is the short chain ester which is providing benefits against soap challenge. Simultaneously, the long chain ester is protecting short chain ester from initial drying effect (FIGS. 2 and 3).

As seen from FIGS. 4, 5, and 6, cetyl lactate alone (long chain ester alone) does not resist increase in dryness upon soap challenge as compared to lactic acid alone which, as would be expected, does resist increase in dryness.

Surprisingly when short chain and long esters are combined, there is also resistance to increase in dryness (see FIG. 5) thereby showing that benefits of short chain ester are achieved while retaining short term moisture benefit of long chain ester.

Lipid Production

With regard to lipid production, lipid analysis of the skin was assessed by measuring the total skin ceramide levels as obtained from tape strips of the skin surface taken at weeks 0 (baseline), 4 and 8 of the study. At a given time, a 3 cm×2 cm piece of Blue Sellotape was applied to the treatment site, pressed firmly onto the skin with the thumbs to ensure adhesion to the skin and was then removed. From the same area, 4 additional strips were taken. These 5 strips were then placed in a given amount of an appropriate extraction solvent (e.g., methanol) and then sonicated or heated slightly while vortexing to release the corneocytes and associated lipids from the tapes. The tape strips were discarded and the extract was analyzed using high performance thin layer chromatography (HPTLC) with densitometry to quantitiate the total ceramide level in that sample.

As seen in FIG. 7, lipid production of long chain ester alone was substantially the same as with vehicle alone. Again, as might be expected, production with lactic acid alone was significantly increased. When combination was used, a directional increase in lipid production was seen at the 80% confidence level. Since increase was apparently not coming from long chain ester (at parity compared to vehicle), it must be coming from short chain ester. Simultaneously, the long chain ester protects against initial drying effect of short chain esters (Example 1).

In addition, it should be noted that an effective lactate dose produced from 1% octyl (S)-lactate is approximately a quarter of that produced from 1.6% (S) lactic acid showing the same trend (lipid production) with even less material used.

In short, both through improvement in barrier function and lipid production, it can be seen that combination of long and short chain esters produced real biochemical improvements in skin condition (presumably through effect of short chain ester not negatively affected when combined with long chain ester). Moreover, the long chain ester masks initial drying effect of short chain ester.

Example 4

Throughout the specification applicants have been talking about the enhanced hydrolysis of short chain esters relative to long chain esters. The following example is shown to demonstrate this effect.

Specifically, a hydrolysis study was conducted as follows:

Hydrolysis Study—Experimental Section

HPLC Method:

Anionic Exclusion Column

Mobile Phase: 100% Water, 0.01% Sulfuric Acid (pH 3)

1.5 mL/min @ 1050 psi, 35° C.

UV @210 nm

The purpose of this study was to utilize High Performance Liquid Chromatography (HPLC) to determine the rates of hydrolysis of alkyl (S)-lactates in the presence of skin enzymes. The method outlined above was used to detect (S)-lactic acid, which elutes off the column at 5.5–5.6 min. The formation of lactic acid is indicative of hydrolysis of the alkyl lactate.

Alkyl lactate was weighed (0.05–0.08 g) and dissolved in sodium phosphate buffer, pH 7.4, in 50 mL volumetric flasks. In the instance of the higher weight alkyl (S)-(S)-lactates, octyl, dodecyl, and octadecyl, they were weighed directly into the HPLC vial using a microbalance.

A calculated amount of the dissolved alkyl lactate was pipetted into a 5 mL volumetric flask to which 1 mL of enzyme solution or buffer (as in the case of assessing chemical hydrolysis) was added. (Note: The enzyme solution is obtained by extracting ground up piglet epidermal skin into an aqueous sodium phosphate buffer). Sodium phosphate buffer was used to dilute the sample up to 5 mL. The amount of alkyl lactate added was calculated such that a 50 ppm concentration of lactic acid would be detected if 100% hydrolysis of the alkyl lactate occurred. Samples were filtered with $0.2\mu$ Acrodisc sterile filters into an HPLC vial.

In the case of octyl, dodecyl, and octadecyl (S)-lactates, 0.8 mL of enzyme or buffer was added and then diluted with 3.2 mL of buffer for a total volume of 4 mL. The weight of the alkyl lactate is considered negligible when regarding the total volume.

An initial injection onto the Anionic Exclusion column was performed after the sample was prepared and was assigned the "time zero" point. The HPLC vial was then wrapped in parafilm and put in a contact temperature water bath 37° C. for a given period of time and then reinjected at various times of the day. The duration in minutes a sample was incubated at 37° C. and the area of the resultant lactic acid peak were recorded.

The amount of lactic acid present in a sample at a specific time was calculated based on a standard curve. The sodium (S)-lactate standards were prepared under identical conditions as the samples themselves, i.e., the appropriate 1 mL of enzyme was added when calculating the amount of lactic acid for enzymatic hydrolysis. For each alkyl (S)-lactate the growth of lactic acid is plotted versus time and compared.

In general, the methodology was based on U. Tauber et al., Pharmacol. Skin, Volume 1, pp. 170–183 (Karger, Basel 1987) which reference is hereby incorporated by reference into the subject application.

It is also possible to monitor the disappearance of the alkyl (S)-lactates using HPLC. However, owing to their different chain lengths they possess different solubility and polarity properties such that more than one method is needed. The ease of using only one method makes the destruction of lactic acid a more favorable route. Also the determination of (S)-lactic acid via HPLC clarifies that the disappearance of the alkyl lactate is due to hydrolysis.

Figure 8:
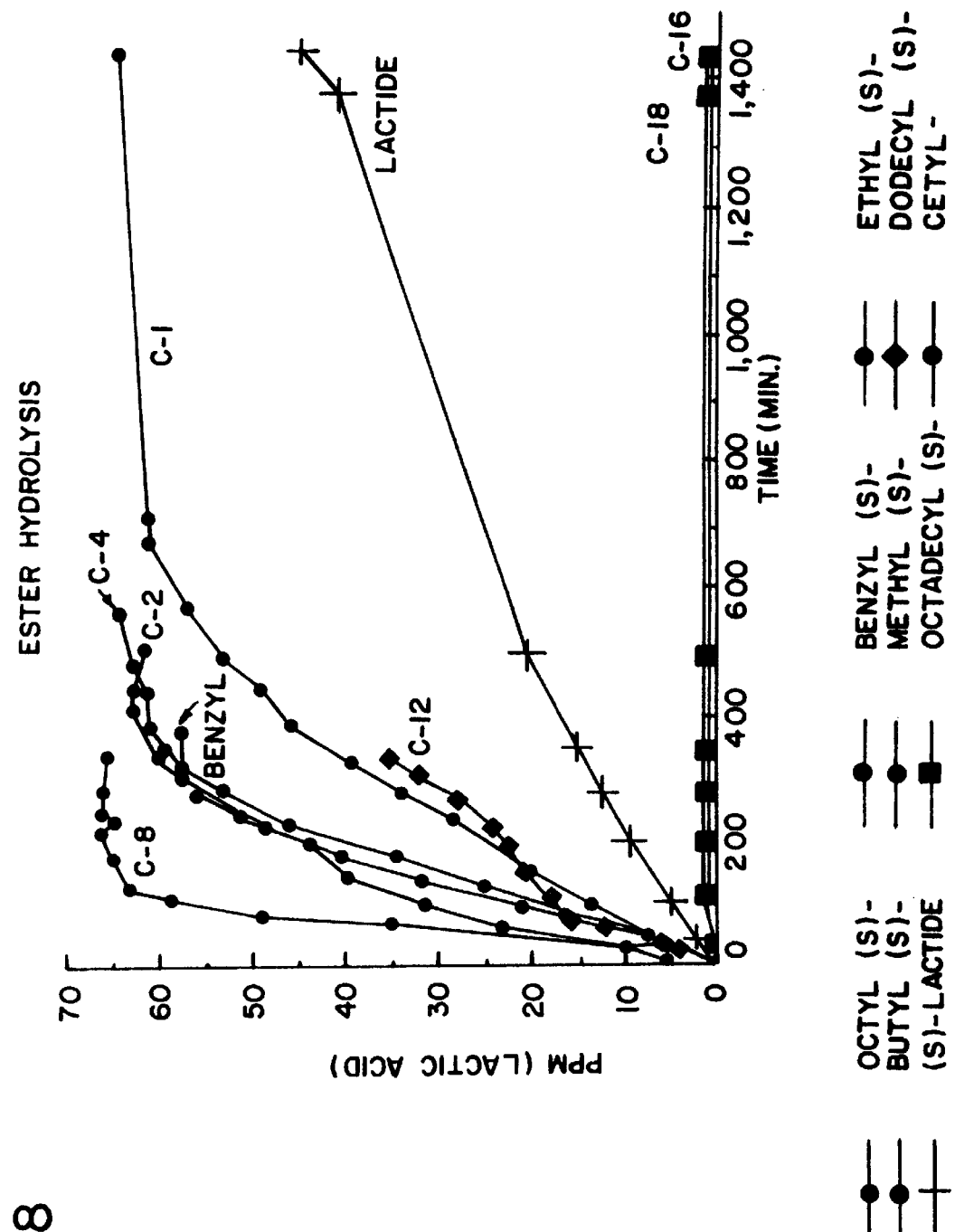
FIG. 8 shows how short chain esters hydrolyze better than long chain esters. It is this efficient hydrolysis which is believed to yield longer term benefits of short chain esters.

Based on the above study, as seen in FIG. 8, it can be seen that short chain esters and in particular $C_8$ esters hydrolyzed far more rapidly than large chain esters such as $C_{16}$ and $C_{18}$ esters. In fact, after 24 hour period, there was little to no hydrolysis observed for $C_{16}$ and $C_{18}$ esters.

To further indicate the differential penetration rates for long chain versus short chain esters, applicants conducted a test in which both octadecyl (S)-lactate (in a vehicle) and octyl (S)-lactate (in water) were applied to skin and measurements were subsequently taken as to how much of the material was left in the upper one-third of the stratum corneum after time.

Specifically, the lactic acid esters; octadecyl (S)-lactate in a vehicle (0.1% glydant plus; 0.4% Pemulen TR2;0.05% DC 190 Silicone; 0.4% Carabopol 980; 0.45% $Na_3PO_4$; 0.24% NaOH; to 100% $H_2O$); and octyl (S)-lactate in water were applied to 72 $cm^2$ area of skin ($\approx 9\mu$ mole/8 $cm^2$). Sellotape strips were used to obtain samples of skin and analysis was conducted by GC/MS.

Figure 9:
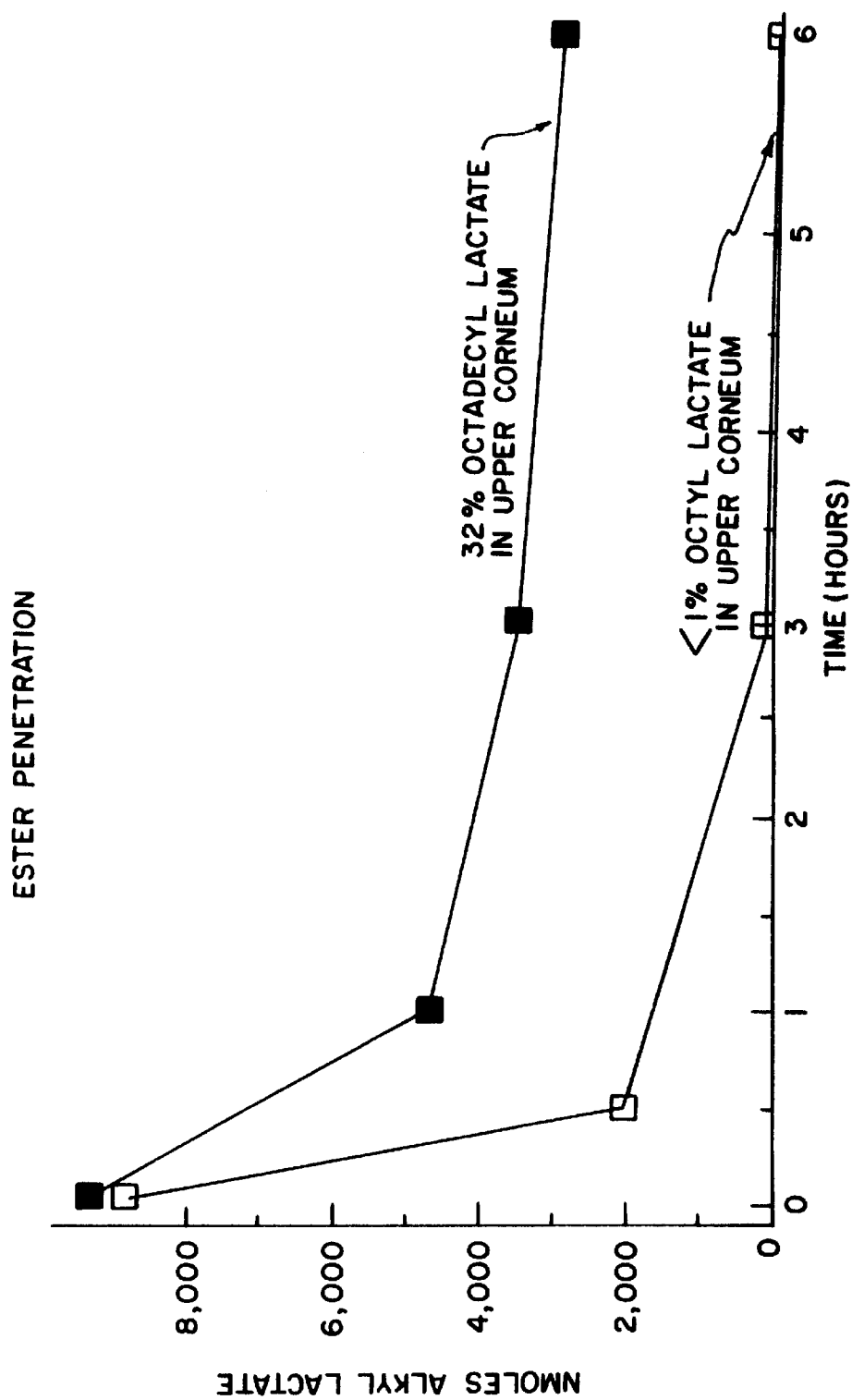
FIG. 9 again shows superior penetration of short term esters versus long chain esters.

As seen from FIG. 9, after six hours almost no product was left when applying short chain esters wherein almost a third of the product remains when applying long chain esters.

This clearly indicates that short chain ester is penetrating the skin at a faster rate than the longer chain ester.

We claim:

1. A composition for application to skin or hair comprising:
   (a) 0 to 90% by wt. surfactant selected from the group consisting of anionic, nonionic, amphoteric, zwitterionic and cationic surfactants; and
   (b) 1% to 25% by wt. of a benefit agent containing composition comprising:
       (i) 0.01 to 10% by wt. of benefit agent selected from the group consisting of butyl lactate and octyl lactate;
       (ii) 0.01% to 10% by wt. of benefit agent selected from the group consisting of cetyl lactate and octadecyl lactate; and
       (iii) balance of composition water.

2. A composition according to claim 1, which is a personal wash composition and comprises 1–20% one or more anionic, 0.1 to 20% amphoteric and 0 to 10% by wt. nonionic.

3. A composition according to claim 2, additionally comprising a structurant.

4. A composition according to claim 3, additionally comprising a thickening or thinning agent.

5. A composition according to claim 2, wherein composition comprises additional oil/emollient.

6. A composition according to claim 1, which is a cosmetic composition and comprises:
   (a) 1 to 25% by wt. total composition benefit agent composition;
   (b) 0 to 30% surfactant;
   (c) 1 to 99% cosmetically acceptable composition.

7. A composition according to claim 6, wherein the cosmetically acceptable composition comprises emollients.

8. A composition according to claim 7, wherein emollients are selected from the group consisting of mono esters, diesters, $C_{16}$–$C_{20}$ fatty acids, $C_{10}$–$C_{20}$ alcohols, linear alkyl polyhydroxide polymeric polyols, branched chain alkyl polyhydroxide polymeric polyols, and $C_{12}$–$C_{30}$ hydrocarbons.

9. A composition according to claim 6, wherein the cosmetically acceptable composition comprises actives selected from the group consisting of sunscreens and tanning agents.

10. A composition according to claim 6, wherein the cosmetically acceptable composition comprises essential fatty acids.

11. A composition according to claim 1, wherein the cosmetically acceptable composition comprises thickener.

* * * * *